US00PP22187P2

(12) United States Plant Patent
Armitage et al.

(10) Patent No.: US PP22,187 P2
(45) Date of Patent: Oct. 4, 2011

(54) ***GAILLARDIA* PLANT NAMED 'GEORGIA YELLOW'**

(50) Latin Name: *Gaillardia×grandiflora*
Varietal Denomination: Georgia Yellow

(75) Inventors: Allan M. Armitage, Athens, GA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/800,579

(22) Filed: May 18, 2010

(51) Int. Cl.
*A01H 5/00* (2006.01)

(52) U.S. Cl. ..... Plt./431

(58) Field of Classification Search ..... Plt./431
See application file for complete search history.

*Primary Examiner* — Annette Para
(74) *Attorney, Agent, or Firm* — Davis Wright Tremaine LLP

(57) ABSTRACT

The new variety 'Georgia Yellow' is provided. The new variety 'Georgia Yellow' generally has brighter yellow flowers and a longer blooming period than similar cultivars of *Gaillardia* plants currently on the market. The new variety 'Georgia Yellow' consistently remains in color throughout the growing season (May-October) of North America.

6 Drawing Sheets

Latin name of the genus and species of the plant claimed: 'Georgia Yellow' is a *Gaillardia* plant that is a hybrid of the genus and species *Gaillardia×grandiflora*.

Variety denomination: The new *Gaillardia* plant claimed is of the variety denominated 'Georgia Yellow'.

BACKGROUND OF THE INVENTION

The present invention relates to the discovery of a new and distinct cultivar of *Gaillardia* plant botanically known as a *Gaillardia×grandiflora* and herein referred to as 'Georgia Yellow', as herein described and illustrated.

The new *Gaillardia* plant variety 'Georgia Yellow' was selected in Watkinsville, Ga. in 2006. The new variety 'Georgia Yellow' generally has brighter yellow flowers and a longer blooming period than similar cultivars of *Gaillardia* plants currently on the market. The new variety 'Georgia Yellow' consistently remains in color throughout the growing season (May-October) of North America.

Pedigree and history: The new *Gaillardia* plant variety 'Georgia Yellow' was one of many seedlings selected in summer 2006 in Watkinsville, Ga. and originated from open pollination of *Gaillardia* plants in the University of Georgia Trial Gardens in Athens, Ga. The maternal plant is likely the *Gaillardia* plant 'Torch Yellow'. Seeds from the open-pollinated *Gaillardia* plants were collected in fall 2005 and grown out in containers and in the field at Watkinsville, Ga. The resulting seedlings, of which the new variety 'Georgia Yellow' was one, were selected in summer 2006. The new *Gaillardia* plant variety 'Georgia Yellow' has been evaluated and tested in Watkinsville, Ga. and Athens, Ga. since 2007.

The new *Gaillardia* plant variety 'Georgia Yellow' has been shown to maintain its distinguishing characteristics through successive asexual propagations by, for example, rooted stem cuttings. Plants from stem cuttings have been directly planted in the ground.

SUMMARY OF THE INVENTION

The new *Gaillardia* plant variety 'Georgia Yellow' has not been observed under all possible environmental conditions.

The phenotype may vary somewhat with variations in environment and cultural practices such as temperature and light intensity without, however, any variance in genotype.

The following traits have been repeatedly observed in Watkinsville and Athens, Ga., and are determined to be the unique characteristics of the new *Gaillardia* plant variety 'Georgia Yellow':

1. Bright yellow flowers that consistently remain in color throughout the growing season (May-October in North America);
2. Long blooming period (at least about 6 months long);
3. Superior landscape performance, illustrating hardiness in U.S. Department of Agriculture (USDA) Zone 7b and possibly perennial in other parts of the U.S.;
4. Compact habit.

The new variety 'Georgia Yellow' can be compared to the *Gaillardia* varieties 'Mesa Yellow' and 'Golden Goblin'.

Comparison to 'Mesa Yellow' (not patented). The new variety 'Georgia Yellow' is more compact in habit than 'Mesa Yellow'. For example, the new variety 'Georgia Yellow' exhibits smaller dimensions in average plant height, flower diameter, leaf length and leaf width than that of 'Mesa Yellow'. In addition, the colors of the flowers of 'Georgia Yellow' are brighter and more eye-catching than those of 'Mesa Yellow.'

Comparison to 'Golden Goblin' (not patented). The new variety 'Georgia Yellow' is more compact in habit than 'Golden Goblin'. For example, the new variety 'Georgia Yellow' exhibits smaller dimensions in average plant height, flower diameter, leaf length and leaf width than that of 'Golden Goblin'. In addition, the colors of the flowers of 'Georgia Yellow' are brighter and more eye-catching than those of 'Golden Goblin.'

BRIEF DESCRIPTION OF THE FIGURES

The accompanying photographic illustration shows typical specimens in full color of the foliage and fruit of the new variety 'Georgia Yellow'. The colors are as nearly true as is reasonably possible in a color representation of this type.

BOTANICAL DESCRIPTION

Figure 1:
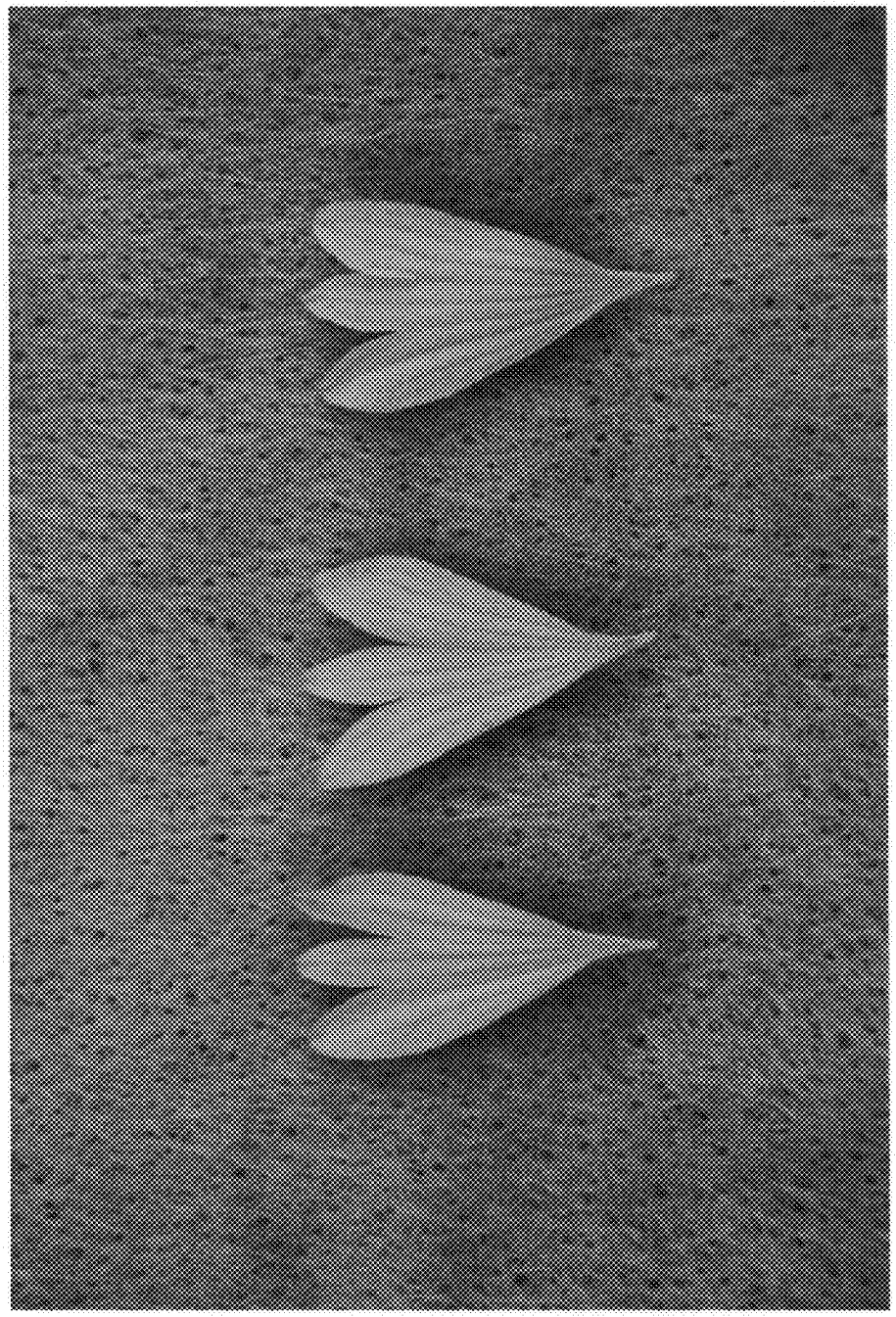
FIG. 1 is a photograph of the petals of the new variety 'Georgia Yellow'.
Figure 2:
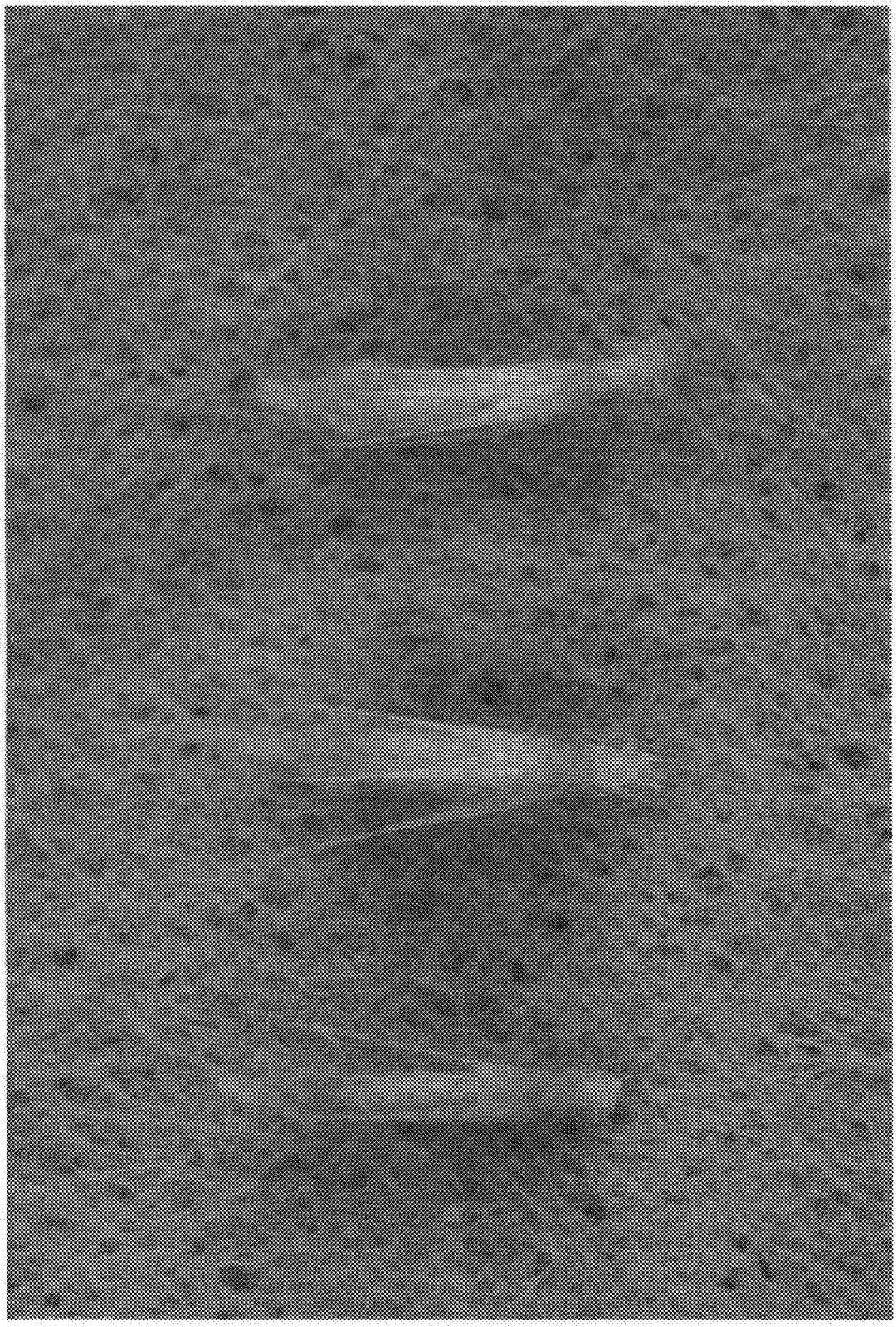
FIG. 2 is a photograph of the stamen of the new variety 'Georgia Yellow'.
Figure 3:
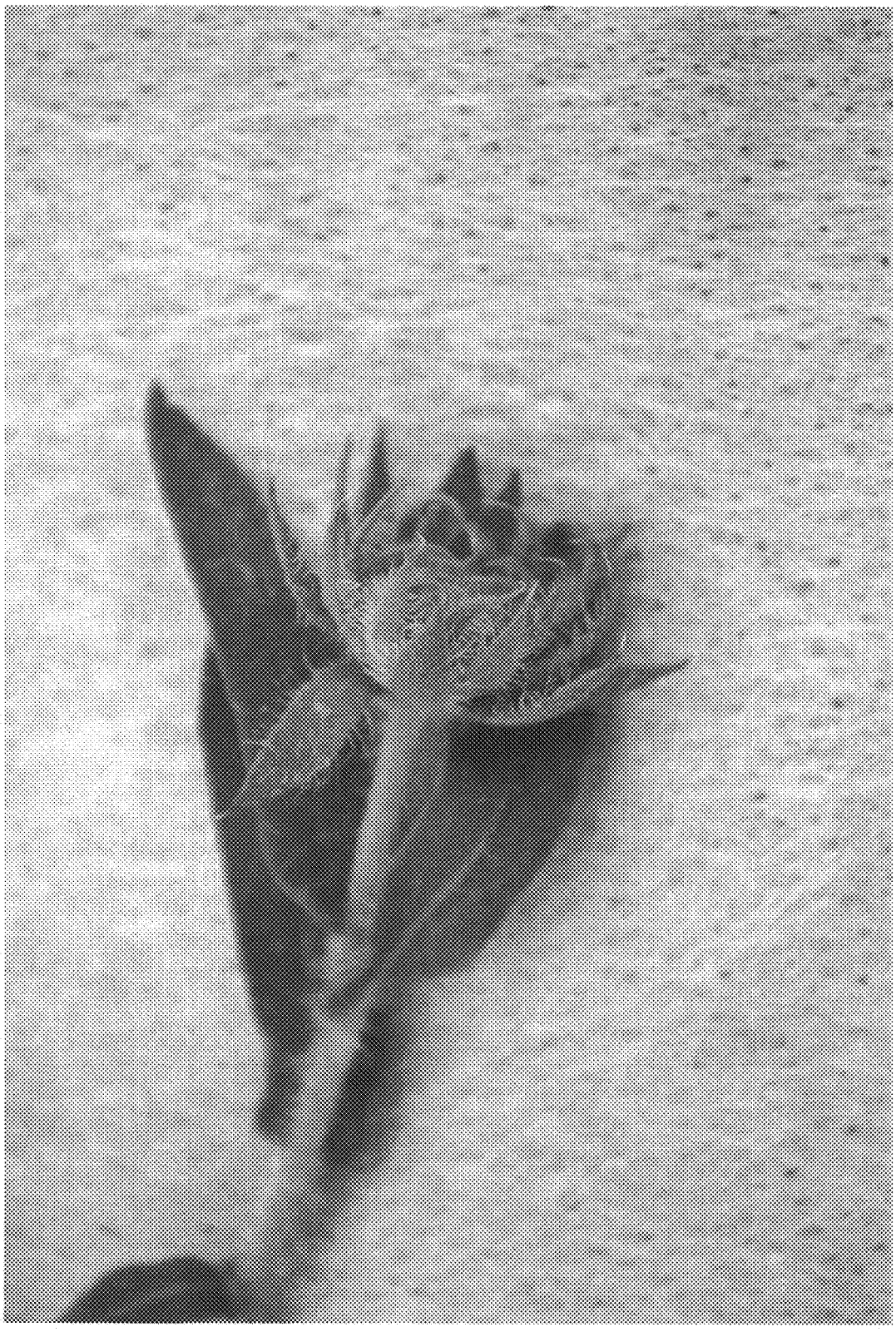
FIG. 3 is a photograph of the sepals and peduncle of the new variety 'Georgia Yellow'.
Figure 4:
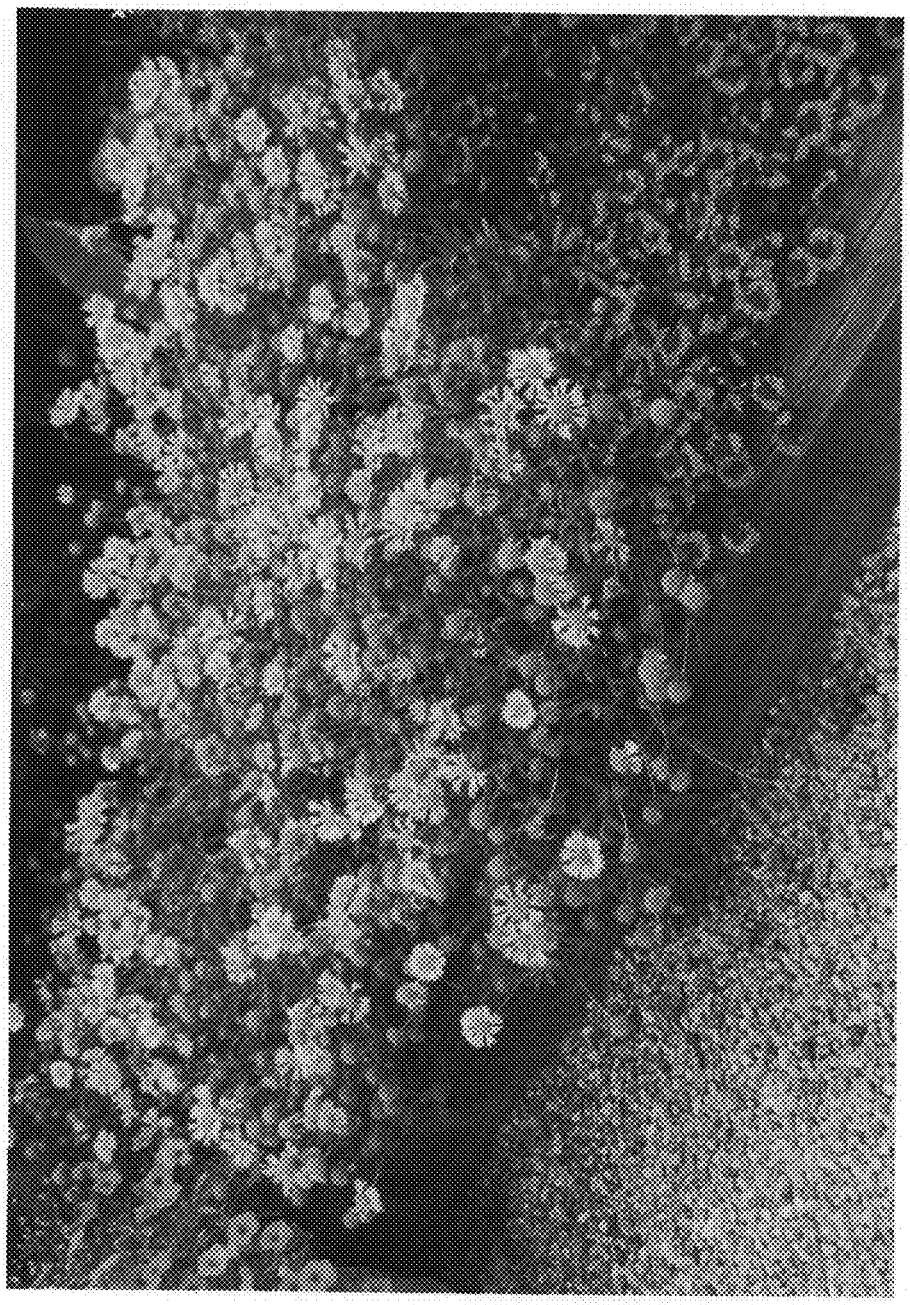
FIG. 4 is a photograph of the new variety 'Georgia Yellow' planted in a garden setting.
Figure 5:
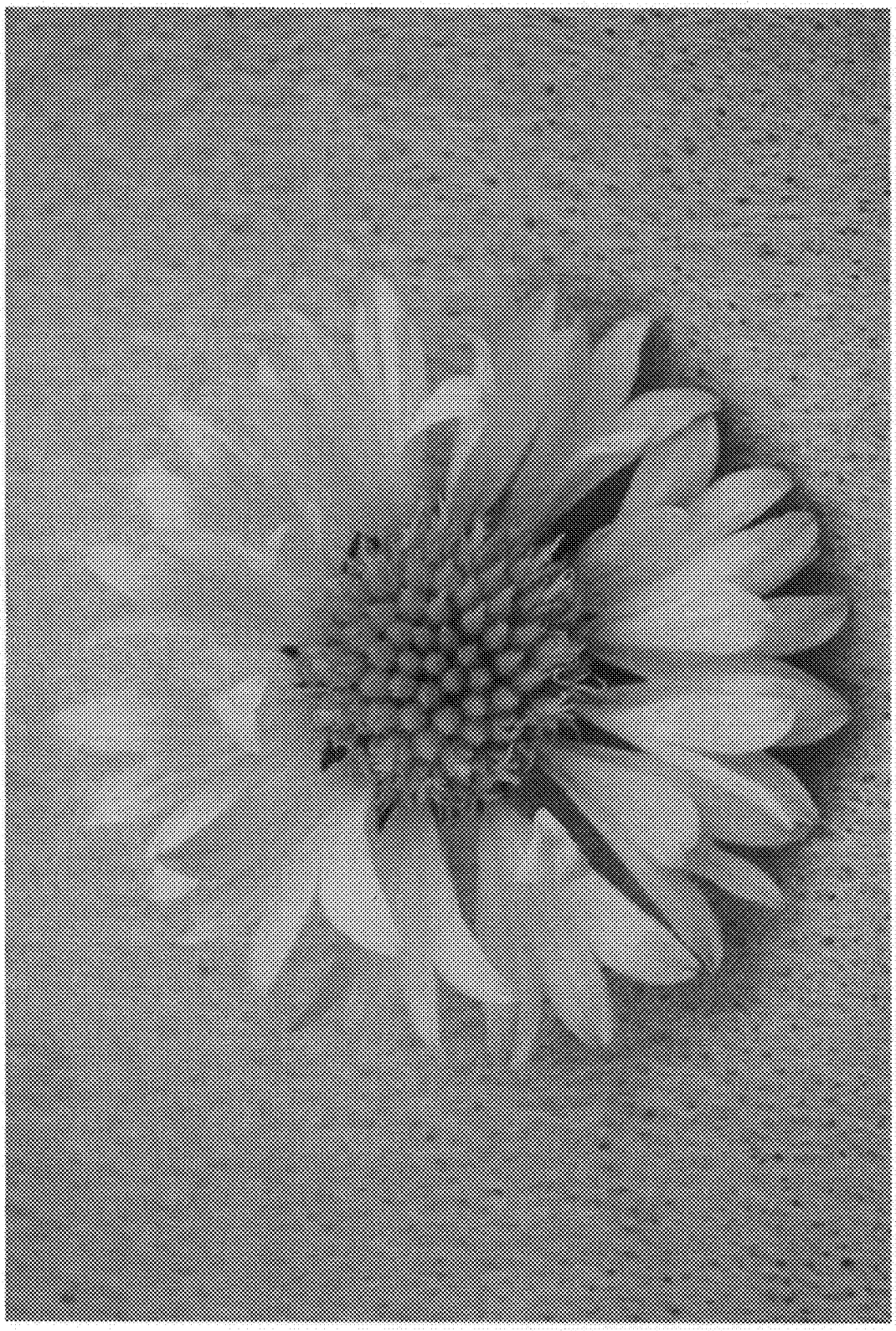
FIG. 5 is a photograph of the flower of the new variety 'Georgia Yellow'.
Figure 6:
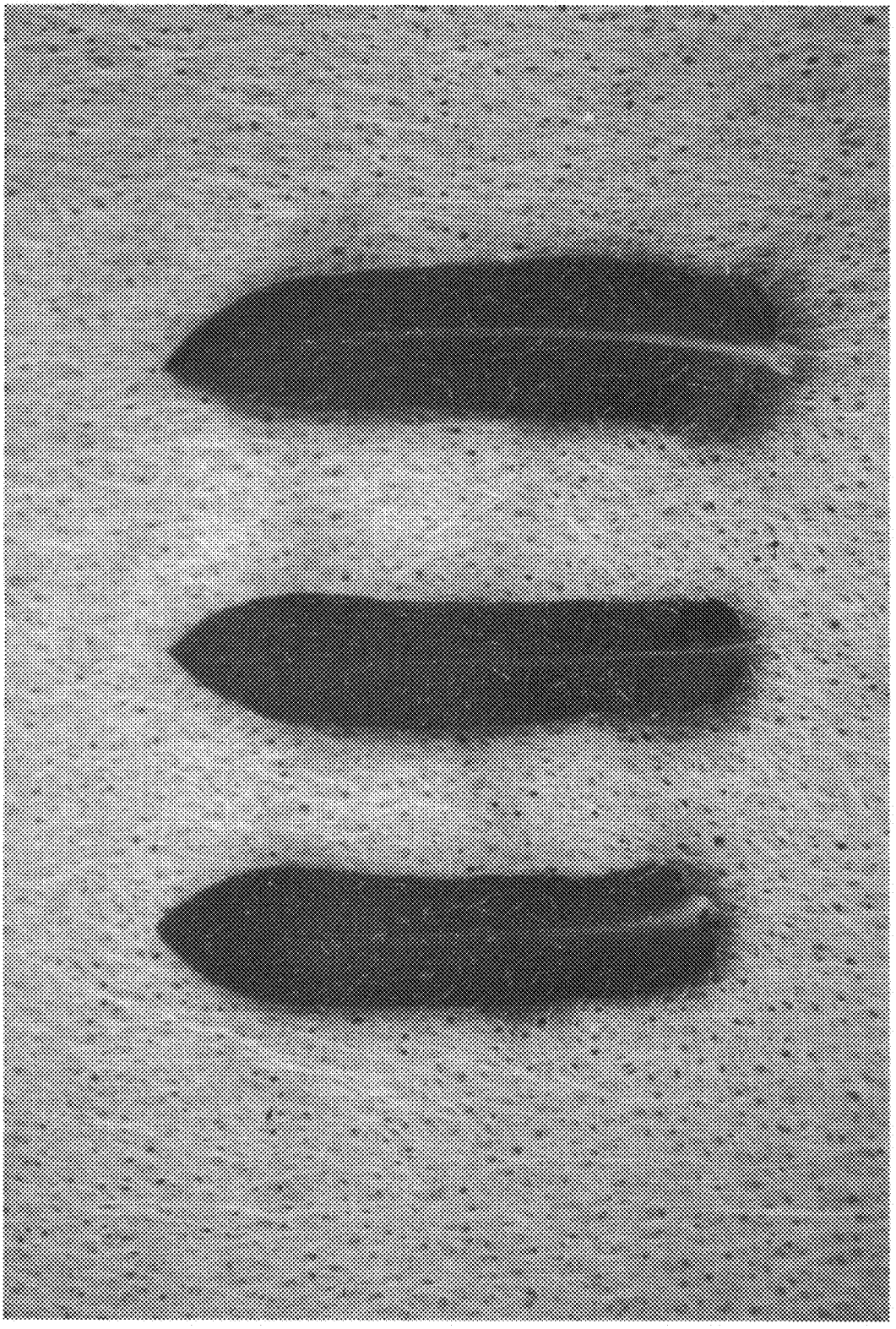
FIG. 6 is a photograph of the leaves of the new variety 'Georgia Yellow'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'Georgia Yellow'. Where dimensions, sizes, colors, and other characteristics are given, it is to be understood that such characteristics are approximations and averages set forth as accurately as practicable. The descriptions reported herein are largely from specimen plants grown in Watkinsville and Athens, Ga. Plants were about 1 to about 3 years old when evaluated.

PLANT

Habit: Mounding to round.
Size: Approximately 38.7 cm tall by about 3 years of age.
Texture: Medium.

STEM

Color: About Moderate yellow green RHS 146C.
Length: Approximately 24.2 cm.
Diameter: Approximately 0.4 cm.
Pubescence: Pilose.
Exfoliation: N/A
Shape: Cylindrical with longitudinal ridges.
Odor: None.
Internode length: Approximately 2.4 cm.

FOLIAGE

Leaf color through seasons: About Dark green RHS 137A.
Length: Approximately 6.1 cm.
Apex: Acute.
Bases: Rounded.
Margin: Entire.
Shape: Elliptical.
*Lobes.*—N/A.
*Sinuses.*—N/A.
Vein color: About Yellow-green RHS 144A.
Pubescence: Pilose.
Leaf arrangement: Alternate.
Leaf venation: Single linear vein.
Texture:
*Thickness.*—Approximately <0.1 mm.
*Degree of waxiness.*—N/A.
Petioles: None.

FLOWER BUDS

Size: Approximately 2.3 cm.
Color: About Yellow-green RHS 145A and RHS 1A both present.
Shape: Accrescent.
Pubescence: Pilose pubescence present on bracts.
Time of full maturity: Summer season.
Time range for showiness: Spring through fall season.

FLOWERS

Inflorescence:
*Type.*—Radiate head.
*Diameter.*—Approximately 6.1 cm.
Flower peduncle:
*Color.*—About Yellow-green RHS 144B.
*Pubescence.*—Pilose.
Flowers per inflorescence: Approximately >100.
Ray flowers:
*Color.*—About Yellow-orange RHS 14A.
*Color at peak of bloom.*—About Yellow-orange RHS 14A on both upper and lower surface.
*Length.*—Approximately 2.3 cm.
*Width.*—Approximately 1.5 cm.
*Apex.*—Lobed.
*Base.*—Attenuate.
*Margin.*—Entire.
*Pubescence.*—None.
*Texture.*—Fine.
Stamen:
*Length.*—Approximately 0.4 mm.
*Width.*—Approximately <0.1 mm.
*Color.*—About Vivid yellow RHS 15A.
*Pollen color.*—About Yellow-orange RHS 17B.
*Pubescence.*—None.
Pistil:
*Shape.*—Y-shaped.
*Length.*—Approximately 0.5 cm.
*Width.*—Approximately 0.1 cm.
*Position.*—Superior.
*Color.*—About Yellow RHS 13C.
*Pubescence.*—None.
Stigma:
*Shape.*—Linear.
*Color.*—About Yellow RHS 13C.
*Pubescence.*—None.
Style:
*Length.*—Approximately 1 cm.
*Shape.*—Linear.
*Color.*—About Yellow RHS 13C.
*Pubescence.*—None.
Ovary:
*Shape.*—Inferior, unilocular with 1 basal ovule.
*Number.*—Approximately 2.
*Pubescence.*—None.

Typical plants of the new variety 'Georgia Yellow' and similar *Gaillardia* varieties ('Mesa Yellow' and 'Golden Goblin') were measured and compared at the University of Georgia Trial Gardens at Athens, Ga. Seedlings of the new variety 'Georgia Yellow' that were selected in 2006 were established in 2006-2007. In late summer 2007, propagules of the new variety 'Georgia Yellow' were grown in the greenhouse and set out in spring 2008 for observation. In 2009, plants of the new variety 'Georgia Yellow' were planted along with the *Gaillardia* varieties 'Mesa Yellow' and 'Golden Goblin'. Plant measurements for each of the varieties are provided in Table 1. The approximate averages of these properties are as follows:

TABLE 1

COMPARISON OF THE NEW VARIETY 'GEORGIA YELLOW' WITH OTHER *GAILLARDIA* PLANT VARIETIES AT ATHENS, GEORGIA

| Cultivar | Plant height (cm)[a] | Flower diameter (cm)[b] | Leaf length (cm)[b] |
|---|---|---|---|
| 'Georgia Yellow' | 38.2 | 6.1 | 4.1 |
| 'Mesa Yellow' | 55.4 | 6.5 | 7.2 |
| 'Golden Goblin' | 60.3 | 6.0 | 5.8 |

| Cultivar | Leaf width (cm)[b] | Flower color[c] | Leaf & stem color[d] |
|---|---|---|---|
| 'Georgia Yellow' | 0.8 | ray: 14C<br>disc: 11A | leaf: 137A<br>stem: 146C |

TABLE 1-continued

COMPARISON OF THE NEW VARIETY 'GEORGIA YELLOW' WITH OTHER *GAILLARDIA* PLANT VARIETIES AT ATHENS, GEORGIA

| | | | |
|---|---|---|---|
| 'Mesa Yellow' | 1.6 | ray: 7A<br>disc: 13A, 155C | leaf; 139B<br>stem: 138B |
| 'Golden Goblin' | 1.1 | ray: 13B<br>disc: 14A, 28C, 155C | leaf: 137B<br>stem: 137A |

[a]Average of 10 measurements from soil to top of flower
[b]Average of 10 measurements
[c]RHS color chart, 2001. More than 1 color may occur on a ray or disc flower, RHS colors range from apex to base of flower
[d]Upper and lower sides of leaves have same RHS color

What is claimed is:

1. A new and distinct variety of *Gaillardia* plant named 'Georgia Yellow', substantially as illustrated and described herein.

* * * * *